United States Patent [19]

Rhodes et al.

[11] Patent Number: 5,681,734
[45] Date of Patent: Oct. 28, 1997

[54] BIOLOGICAL CONTROL AGENT

[75] Inventors: David John Rhodes, Crowthorne; Philippa Jane Guest, Maidens Green, both of United Kingdom; Robert Gerard Blenk, Raleigh, N.C.

[73] Assignee: Zeneca Limited, London, United Kingdom

[21] Appl. No.: 337,360

[22] Filed: Nov. 10, 1994

[30] Foreign Application Priority Data

Nov. 15, 1993 [GB] United Kingdom ............... 9323495

[51] Int. Cl.$^6$ .................. C12N 7/00; C12N 7/02; A01N 63/00
[52] U.S. Cl. ............. 435/235.1; 435/239; 435/240.2; 424/93.6; 504/117
[58] Field of Search ............ 424/93.6; 435/235.1, 435/239, 240.2; 504/117

[56] References Cited

U.S. PATENT DOCUMENTS

| | | | |
|---|---|---|---|
| 4,911,913 | 3/1990 | Hostetter et al. | 424/93.6 |
| 5,023,182 | 6/1991 | Vail | 435/235.1 |
| 5,132,220 | 7/1992 | Shapiro et al. | 435/235.1 |
| 5,298,418 | 3/1994 | Granados | 435/240.2 |

FOREIGN PATENT DOCUMENTS

90/10387  9/1990  WIPO .

*Primary Examiner*—Blaine Lankford
*Attorney, Agent, or Firm*—Melissa A. Shaw; Marian T. Thomson

[57] ABSTRACT

An isolated nuclear polyhedrosis virus strain having the characteristics of the sample deposited in the European Collection of Animal Cell Cultures under accession number V93071301.

5 Claims, 1 Drawing Sheet

BIOLOGICAL CONTROL AGENT

This invention relates to a previously unisolated and unidentified strain of an entomopathogenic virus and to biological control agents comprising it and to its replication and use in the control of insect pests.

BACKGROUND TO THE INVENTION

The nuclear polyhedrosis viruses are insect-specific DNA viruses of the family Baculoviridae, in which enveloped rod-shaped nucleocapsids, containing a circular double-stranded DNA genome ranging from 50 to 100M daltons in size, are occluded within a protein matrix known as a polyhedron. NPVs may be singly-embedded (SNPV) or multiply-embedded (MNPV), according to the number of nucleocapsids per envelope. Because these viruses are pathogenic to several of the major lepidopteran pests of agricultural crops and forestry, they have been intensively studied as biological pest control agents. Although they have been sold commercially for this purpose, the widespread use of such products has been limited by their poor persistence, slow speed of kill, and high cost per unit area treated.

SUMMARY OF THE INVENTION

A new strain of singly-embedded *Heliothis zea* nuclear polyhedrosis virus (HzSNPV) is described, deposited in the European Collection of Animal Cell Cultures under the accession number V93071301. It is characterised by high virulence, which provides an advantage over existing strains. Thus, according to one aspect of the present invention there is provided an isolated nuclear polyhedrosis virus strain having the characteristics of the sample deposited in the European Collection of Animal Cell Cultures, U.K., under accession number V93071301.

The virus may be used for control of pest species such as species of the genera *Heliothis* and *Helicoverpa*, for example when formulated as an agricultural spray. Thus, according to other aspects of the present invention there is provided a biological control agent comprising the virus of the present invention, and a method of combating an insect pest at a locus which comprises treating the insect or locus with the biological control agent of the present invention.

The present ivention also provides a method for the in vitro replication of the virus of the present invention comprising infecting a culture of insect cells in a medium with the virus, culturing the cells for a period until polyhedral inclusion bodies are detected within the nuclei of the cells, and harvesting the virus from cells and/or the medium.

DETAILED DESCRIPTION OF THE INVENTION

Isolation

The virus was originally propagated from three dead larvae of *Helicoverpa zea*, discovered in Pikeville, N.C., U.S.A. The virus was propagated by transferring cadavers into plastic cups containing freshly-prepared insect diet, crushing the cadaver on the surface of the diet, and introducing a larva of *Heliothis virescens* or *Helicoverpa zea* which was allowed to feed on the contaminated diet. Infection was normally carried out at 20°–25° C. Propagation was carried out at intervals varying between two weeks and one year. Cadavers were stored in plastic diet cups at ambient temperature.

Purification

The virus was propagated in *Heliothis virescens* as described above. Symptoms were consistent with those of virus infection. Infected larvae became flaccid, blackened, and tended to rupture and liquefy. Inoculum of the pathogen was produced by further transfers to diet, by streaking the surface of the diet with a sterile plastic loop containing tissue from diseased insects. Cadavers were stored at −20° C. Fifty infected larvae were obtained in this way.

The cadavers were collected, triturated in sterile distilled water, and filtered through two layers of muslin. The filtrate was repeatedly centrifuged at 1000 rpm for five minutes to remove insect debris. The supernatant was then centrifuged at 4,100 rpm for 20 minutes, and the pellet retained after washing. The pellet was resuspended in water and examined under the microscope. Particles typical of a nuclear polyhedrosis virus (NPV) were observed. Approximately $5 \times 10^7$ polyhedral inclusion bodies (PIB) were obtained per larva.

A sample of the virus was deposited in the European Collection of Animal Cell Cultures, PHLS, Salisbury, Wilts. SP4 0JG, U.K. under the accession number V93071301 on Jul. 13, 1993.

Bioassay

For purposes of comparison, the virus was bioassayed together with a characterised strain of *Heliothis armigera* nuclear polyhedrosis virus, HaSNPV A44EB, which had previously been shown to infect *Heliothis virescens*, *Helicoverpa zea*, *Helicoverpa armigera* and *Helicoverpa punctigera*. This strain had been cloned from an isolate collected by Dr. Robert Teakle from infected *Helicoverpa armigera* on cotton in Queensland, Australia in 1974.

Plugs of pinto bean insect diet, approximately 1 mm in diameter, were placed in wells of microtitre dishes. Polyhedra, at varying concentrations, were then applied to the surface of each plug in a volume of 1 μl water. After 24 hours, all larvae which had consumed the diet plugs were transferred to plastic pots containing diet. The insects were examined after seven days.

The results are set out in Table I below.

It is evident that HzNPV V93071301 is more virulent by at least an order of magnitude than HaSNPV A44EB against at least *H. virescens* and *H. zea*.

Although HzNPV V93071301 was not compared directly with a commercial standard, HaSNPV A44EB had been shown in a similar test to be as or slightly more virulent than the "Elcar" commercial strain of HzSNPV against *Heliothis virescens* as set out in Table 2 below. "Elcar" is a Registered Trade Mark.

TABLE I

Comparative bioassay data on HzSNPV V93071301 and HaSNPV A44EB.

| TEST INSECT | TEST NUMBER | VIRUS | LC$_{50}$ and 95% confidence interval at 7 days after treatment (PIB/ml) |
|---|---|---|---|
| Heliothis virescens | 1 | HaSNPV A44EB | 7573 (4496–12624) |
| | | HzSNPV V93071301 | 596 (268–1192) |
| | 2 | HaSNPV A44EB | 1603 (0–25994) |
| | | HzSNPV V93071301 | 126 (34–275) |
| | 3 | HaSNPV A44EB | 6532 (3940–11262) |
| | | HzSNPV V93071301 | 18 (0–92) |
| | 4 | HaSNPV A44EB | 2363 (951–4779) |
| | | HzSNPV V93071301 | 506 (76–1238) |
| Helicoverpa zea | 1 | HaSNPV A44EB | 1745 (242–7341) |
| | | HzSNPV V93071301 | 111 (59–178) |

TABLE II

Comparative bioassay data on HaSNPV A44EB and HzSNPV "Elcar" strain vs *Heliothis virescens*

| TEST NUMBER | VIRUS | LC$_{50}$ and 95% confidence interval at 7 days after treatment (PIB/ml) |
|---|---|---|
| 1 | HzSNPV "Elcar" | 4309 (1440–13315) |
| | HaSNPV A44EB | 3329 (977–10386) |
| 2 | HzSNPV "Elcar" | 2713 (1504–4815) |
| | HaSNPV A44EB | 2567 (1008–9667) |

Cell Culture

HzNPV V93071301 was established in cell culture by extracting hemolymph from infected insects into a static culture of *Helicoverpa zea* cells. The virus successfully infected the cells, forming polyhedra within the nucleus, and could be propagated in cell culture. Plaques were formed in a confluent layer of *H. zea* cells when exposed to the non-occluded form (NOV) of HzNPV V93071301.

Identification

Infected insects were triturated in an aqueous solution of 1% sodium dodecyl sulphate (SDS). The suspension of polyhedra was adjusted to approximately 5×10$^9$ PIB per sample, filtered, centrifuged, and washed as described previously, removing the SDS. Polyhedra were then dissolved in a solution of Na$_2$CO$_3$ buffer at pH10. The suspension was centrifuged at 5000 rpm for five minutes to remove debris, and the supernatant centrifuged at 14000 rpm for 45 minutes. The virions were resuspended in 200 µl of TE (Tris HCl at 10 mM, EDTA at 1 mM) at pH8. Proteins were digested by adding to the virus preparation 200 µl of extraction buffer (0.2% w/v KCl, 0.2% sarcosyl in TE) followed by proteinase K to a final concentration of 0.1 mg/ml. The digest was incubated for 3–4 hours at 65° C. with gentle agitation, mixed with 400 µl phenol/CHCl$_3$/isoamyl alcohol (50:48:2) and centrifuged for five minutes at 13000 rpm. This extraction was performed twice. Excess salts, detergents, phenol and chloroform were removed by dialysis for approximately 12 hours. The DNA preparations were then digested for 5 to 6 hours with each of the restriction endonucleases EcoRI, EcoRV, HindIII and BamHI. The DNA preparations were analysed by agarose gel electrophoresis (0.7–0.8% agarose). Samples of HzNPV V93071301, HaSNPV A44EB, and HaSNPV "Elcar" were run simultaneously. The number of bands which were observed in total for each virus, and the number of identical bands which were observed between pairs of viruses, is listed in Table 3.

TABLE III

Identity of virus strains according to agarose gel electrophoresis

| VIRUS 1 | TOTAL NUMBER OF BANDS OBSERVED | VIRUS 2 | NUMBER OF BANDS IDENTICAL WITH THOSE OF VIRUS 1 |
|---|---|---|---|
| HaSNPV "Elcar" | 58 | HaSNPV | 48 |
| HaSNPV "Elcar" | | HzNPV V93071301 | 49 |
| HaSNPV A44EB | 55 | HaSNPV "Elcar" | 48 |
| HaSNPV A44EB | | HzNPV V93071301 | 47 |
| HzNPV V93071301 | 53(+1 faint band) | HaSNPV "Elcar" | 49 |
| HzNPV V93071301 | | HaSNPV A44EB | 49 |

It is evident that, while there is sufficient homology between these viruses to classify HzNPV V93071301 as a singly-embedded *Heliothis zea* nuclear polyhedrosis virus (HzSNPV), strain V93011301 is clearly distinct, according to DNA profile, from either of the other strains which were tested.

BRIEF DESCRIPTION OF THE DRAWINGS

Further evidence of the novelty of the strain of the present invention can be seen from FIG. 1 which shows an electron micrograph of a section of a polyhedron from the virus of the present invention. In order to obtain the electron micrograph, a sample was fixed in 3% gluteraldehyde in 0.05M phosphate buffer for 16 hours at 4° C., postfixed in 1% osmium texroxide in 0.05M phosphate buffer, set in agarose gel, dehydrated and infiltrated. The sample was then set in Spurr's resin. Ultrathin sections (about 70–90 nm) were stained with 0.2% lead citrate in 0.1N sodium hydroxide for 5 minutes. The sections were examined using a Phillips PW 6002 Transmission Electron Microscope.

Formulation and Use

Figure 1:
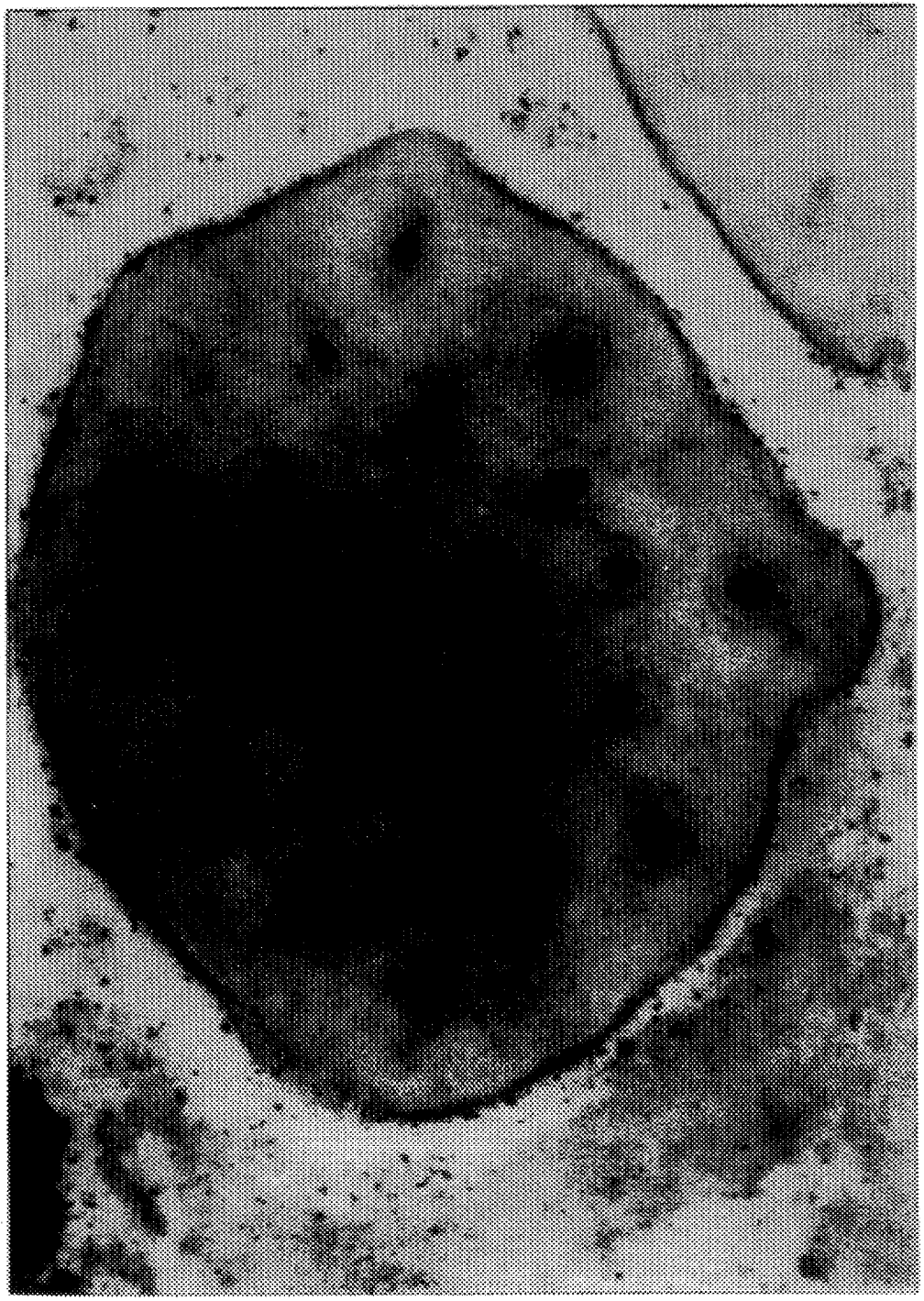

The novel virus strain of the invention is suitable for use as a biological control agent for the control of insect pests, particularly larval lepidopterous pests of agriculturally useful crops, such as cotton, vegetables, friut, soya, cereals and the like. Amongst pests which may be combated and controlled by the use of the virus are *Heliothis* and *Helicoverpa* spp. such as *H. zea, H. virescens, H. armigera, H. punctigera* and the like.

The virus is applied to the pests or the locus of the pests (e.g. a growing crop) in the form of a composition in which the virus is admixed with suitable diluents or carriers which may be solid or liquid, optionally in the presence of additional ingredients such as surfactants, wetting and dispersing agents, and ingredients intended to protect the viability of the virus such as U.V. absorbents, antioxidants and the like. Preferred formulations include wettable powders, oil suspensions, and microcapsulated suspensions of the virus (e.g. wherein the capsule coat is obtained by a coascervation technique or by in-situ cross-linking to form a polyurea or polyamide shell). A fuller disclosure of the techniques of formulation of nuclear polyhedrosis viruses for use as biological control agents is provided by D J Rhodes in "Formulation of Biological Control Agents" in "Exploitation of Microorganisms" edited by D G Jones, 1993 Chapman & Hall, London) at pages 411–439, and the references cited therein.

What is claimed is:

1. An isolated singly-embedded nuclear polyhedrosis virus strain having all the identifying characteristics of the sample deposited in the European Collection of Animal Cell Cultures under accession number V93071301.

2. A biological control agent comprising the virus of claim 1 in association with a solid or liquid diluent or carrier.

3. A method of combating an insect pest wherein the insect pest is of the genera *Heliothis* or *Helicoverpa* at a locus, which comprises treating the pest or the locus with the biological control agent of claim 2.

4. A method according to claim 3 wherein the insect pest is *H. zea, H. virescens, H. armigera* or *H. punctigera*.

5. A method for the in vitro replication of the virus of claim 1 which comprises infecting a culture of *Helicoverpa* insect cells in a medium with the virus, culturing the cells for a period until polyhedral inclusion bodies are detected within the nuclei of the cells, and harvesting the virus from the cells of the medium.

* * * * *